United States Patent
Rapkin et al.

[11] Patent Number: 5,296,377
[45] Date of Patent: Mar. 22, 1994

[54] CONTROL REAGENT CONTAINING A HYDROXYLAMINE OR AN ANTIOXIDANT

[75] Inventors: Myron Rapkin, Indianapolis; David Tabb, Greenfield; Eric Diebold, Fishers, all of Ind.

[73] Assignee: Boehringer Mannheim Corporation, Indianapolis, Ind.

[21] Appl. No.: 990,433

[22] Filed: Dec. 15, 1992

[51] Int. Cl.$^5$ .................. G01N 31/00; G01N 33/66
[52] U.S. Cl. .......................... 436/13; 436/14; 436/16; 436/18; 436/95; 436/106; 252/408.1
[58] Field of Search ............ 436/8, 11, 12, 13, 14, 436/15, 16, 18, 106, 95; 252/408.1

[56] References Cited

U.S. PATENT DOCUMENTS

| | | | |
|---|---|---|---|
| 3,260,648 | 7/1966 | Fox | 167/84 |
| 3,274,062 | 9/1966 | Lou | 167/84.5 |
| 3,466,249 | 9/1969 | Anderson | 252/408 |
| 3,852,415 | 12/1974 | Vandervoorde | 424/1 |
| 3,859,047 | 1/1975 | Klein | 23/230 |
| 3,920,400 | 11/1975 | Scheibe et al. | 23/230 |
| 3,920,580 | 11/1975 | Mast | 252/408 |
| 3,973,913 | 8/1976 | Louderback | 23/230 |
| 4,054,488 | 10/1977 | Marbach | 195/1.8 |
| 4,078,892 | 3/1978 | Steinbrink, Jr. | 23/230 |
| 4,121,905 | 10/1978 | Maurukas | 23/230 |
| 4,123,384 | 10/1978 | Hundt et al. | 252/408 |
| 4,126,575 | 11/1978 | Louderback | 252/408 |
| 4,127,502 | 11/1978 | Li Mutti et al. | 252/408 |
| 4,193,766 | 3/1980 | Daunora et al. | 23/230 |
| 4,199,471 | 4/1980 | Louderback et al. | 252/408 |
| 4,230,601 | 10/1980 | Hill | 252/408 |
| 4,260,579 | 4/1981 | Barton et al. | 422/56 |
| 4,276,376 | 6/1981 | Hundt et al. | 435/17 |
| 4,298,498 | 11/1981 | Rehner et al. | 252/408 |
| 4,301,028 | 11/1981 | Bartl et al. | 252/408 |
| 4,372,874 | 2/1983 | Modrovich | 436/176 |
| 4,405,718 | 9/1983 | Rapkin et al. | 436/8 |
| 4,438,202 | 3/1984 | Engler et al. | 436/8 |
| 4,529,704 | 7/1985 | Trimmer et al. | 436/14 |
| 4,554,249 | 11/1985 | Kosaka et al. | 435/10 |
| 4,643,976 | 2/1987 | Hoskins | 436/15 |
| 4,678,754 | 7/1987 | Hoskins | 436/15 |
| 4,729,959 | 3/1988 | Ryan | 436/14 |
| 4,839,279 | 6/1989 | Kosaka et al. | 435/25 |
| 5,028,542 | 7/1991 | Kennamer et al. | 436/14 |
| 5,149,321 | 9/1992 | Klatz et al. | 604/52 |

Primary Examiner—James C. Housel
Assistant Examiner—N. Bhat
Attorney, Agent, or Firm—Felfe & Lynch

[57] ABSTRACT

Control reagents an oxidant or a hydroxylamine compound together with other ingredients, the most important of which is a known amount of the analyte for which the reagent acts as a control.

17 Claims, 6 Drawing Sheets

CONTROL REAGENT CONTAINING A HYDROXYLAMINE OR AN ANTIOXIDANT

FIELD OF THE INVENTION

The invention relates to control reagents. More particularly, it relates to control reagents formulated so as to improve the stability of the analytes contained therein, without affecting the usefulness of the composition.

BACKGROUND AND PRIOR ART

Work in clinical analysis requires the investigator to evaluate a given sample to determine whether a particular analyte of interest is present, and if so, in what amount. Such information is extremely valuable in diagnosis and treatment of patient. The analyses referred to supra are being carried out, more and more frequently, using automated methods. These methods are diverse, but generally involve the preparation of a sample which is then introduced to an automatic analyzer. The analyzer is set up to carry out various reactions designed to measure the analyte or analytes of interest, and to determine a particular value or "signal" associated with these reactions. Sophisticated automated systems convert these reading into a value indicative of the analyte's presence or concentration, thereby providing the investigator with a precise determination of the particular analyte of interest.

The analytical systems outlined supra, as well as any analytical system used for clinical purposes requires that a control be used. Such controls permit the investigator to check the accuracy of the system being used. In clinical diagnosis where some analytes are present in only vanishingly small amounts, and where minute changes in levels mean the difference between normal and pathological conditions, a satisfactory control reagent becomes an integral, and critical part of the analytical system.

Control reagents should be as similar to the sample type for which they serve as a control as possible. Biological fluids such as blood and serum, e.g., are extremely complex compositions, however, and there are many examples of formulations designed to be as close as possible to biological fluids and to serve as controls therefor. A cursory sampling of the patent literature in this area includes, e.g., U.S. Pat. Nos. 4,678,754 (Hoskins); 4,643,976 (Hoskins); 4,529,704 (Tremner et al.); 4,438,702 (Engler et al.); 4,405,718 (Rapkin et al.); 4,372,874 (Modrovich); 4,301,028 (Barth et al.); 4,276,376 (Hundt et al.); 4,260,579 (Barton et al.); 4,230,601 (Hell); 4,199,471 (Louderback et al.); 4,193,7666 (Dounora et al.); 4,127,502 (Li Mutti et al.); 4,126,575 (Louderback); 4,123,384 (Hundt et al.); 4,121,905 (Maurukas): 4,054,488 (Marbach); 4,078,892 (Steinbrink, Jr); 3,973,913 (Louderback); 3,920,580 (Mast); 3,920,400 (Scheibe et al.); 3,859,047 (Klein); 3,466,249 (Anderson); 3,852,415 (Vandervoorde); 3,274,062 (Lou); 3,260,648 (Fox). The approaches taken in these patents vary. Many of them teach control reagents useful for determining one, or a family of a few related analytes. Others are more general, and relate to improvements in the field in general. It is the latter group to which the present invention belongs.

As was noted supra, attempts are made within the art to formulate control reagents that are as close to the type of material for which they are controls as possible. As a result, control reagent are frequently based upon blood, plasma, or serum, be these human or mammalian (e.g., bovine).

Control reagents of the type discussed supra do have certain drawbacks, which are inherent in any natural product based material. For this, and other reasons, the art has also contemplated and used control reagents which are serum free. Generally, these water based control reagents have to be substantially modified so as to make them as close to a biological sample as possible. An example of such a modification is the inclusion of a polymeric viscosity agent, to make the reagents' rheological properties as close to biological samples as possible.

A major problem with all control reagents is the tendency of the analyte of interest to undergo chemical reactions in situ, thereby leading to false results when the control is in fact used. An example of such a chemical reaction is simple oxidation. Oxidized analyte, or analyte which otherwise reacts prior to use of the control system, leads to shifts in signal formation and away from true control values. Generally, these controls produce a greater signal than a corresponding amount of analyte in a sample being analyzed.

It has now been found, surprisingly, that control reagents can be prepared where the problem alluded to supra is avoided, without any disruption in the chemistry of the stabilized system. The invention, elaborated upon more fully infra, involves the incorporation of at least one antioxidant or one hydroxylamine into a liquid based control reagent which also contains a known amount of at least one analyte. The resulting material, referred to hereafter as a stabilized control reagent, is useful in the same way any control reagent is useful.

DETAILED DESCRIPTION OF PREFERRED EMBODIMENTS

In the examples which follow, the material SERASUB TM is used. SERASUB TM is a commercially available, synthetic serum substitute; however, its composition is proprietary to the manufacturer and is unknown to the inventors, and thus is not reported herein. Additional information and examples are provided using different media, it being understood, however, that SERASUB is the preferred, but not required medium. The examples provided using SERASUB are presented to satisfy the best mode requirement.

EXAMPLE 1

A glucose control reagent was prepared using "stripped" bovine serum. This material has its cholesterol removed, and contains a predetermined amount of glucose.

The control material was combined with 100 mg/dl of N-t-butyl hydroxylamine HCl, to prepare a control reagent. This material was then tested against samples of capillary blood, which had been adjusted to contain a known amount of glucose. Both the controls and blood samples were tested in the same analytical apparatus, using an indicator system which employs the well known hexokinase assay system for measuring glucose.

Figure 1:
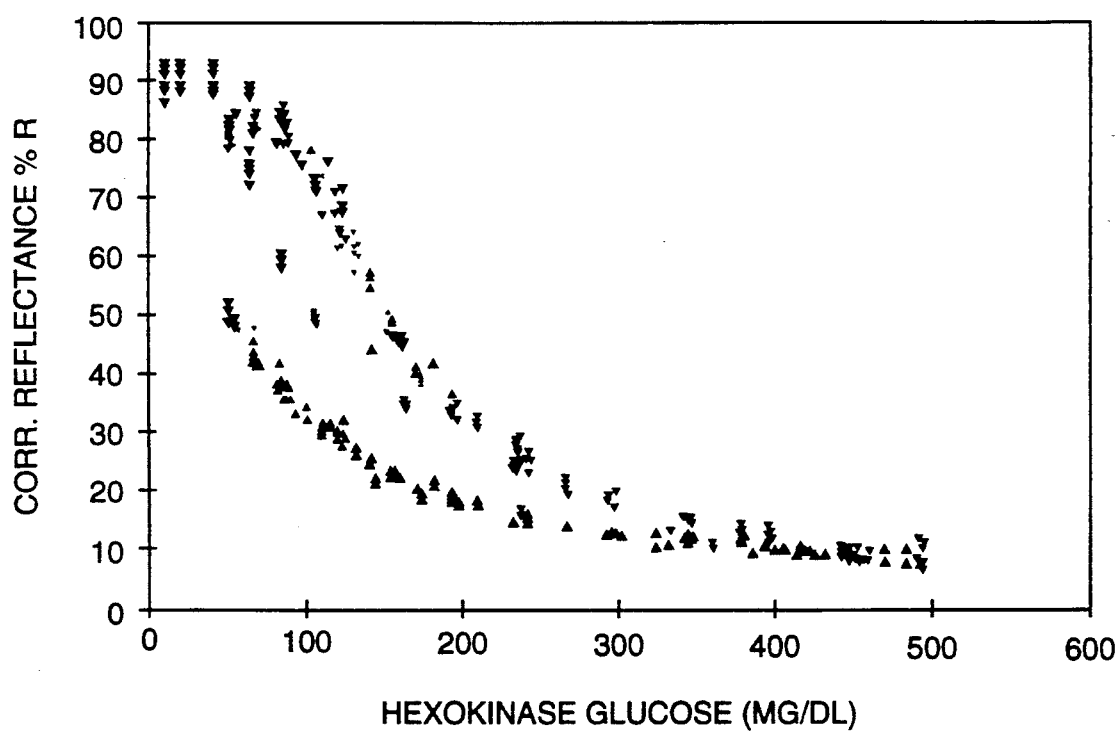
FIG. 1 presents a correlation curve between a bovine serum based control reagent and capillary blood.

A correlation curve is presented as FIG. 1. It shows that the control reagent described herein behaved very similarly to capillary blood under the conditions described, indicating that the material was useful as a control reagent.

EXAMPLE 2

A control reagent based upon plasma was used, the formulation of which was as follows:

| pH (1% soluton in 0.15 M NaCl) | | |
| --- | --- | --- |
| pH | 7.6 | |
| Absorbance | | |
| Absorbance at 710 nm | 0.0 | |
| Absorbance at 570 nm | 0.2 | |
| Protein | | |
| Protein | 15. | % |
| Electrolyte analysis | | |
| Sodium | 67 | mEa/L |
| Potassium | 0.6 | mEa/L |
| Chloride | 11. | mEa/L |
| Results from a sample diluted to 7.3% protein in 0.9% (0.15 M) saline: | | |
| Cholesterol @ 7.5% protein | | |
| Cholesterol | 111. | MG/DL |
| Iron @ 7.0% protein | | |
| Iron | 102. | us/dL |
| A/G ratio | | |
| A/G ratio | 1.2 | |
| Glucose | 2. | ms/dL |
| BUN | 0. | ms/dL |
| Creatinine | 0.0 | ms/dL |
| Uric acid | 0.0 | ms/dL |
| Albumin | 4.0 | s/dL |
| Globulin | 3.3 | s/dL |
| Calcium | 0.9 | ms/dL |
| Inorganic phosphorous | 0.1 | ms/dL |
| Triglycerides | 2. | ms/dL |
| Alkaline phosphatease | 0. | u/L |
| SGOT | 0. | u/L |
| SGPT | 4. | u/L |
| LDH | 17. | u/L |
| Total bilirubin | 0.1 | ms/dL |

Figure 2:
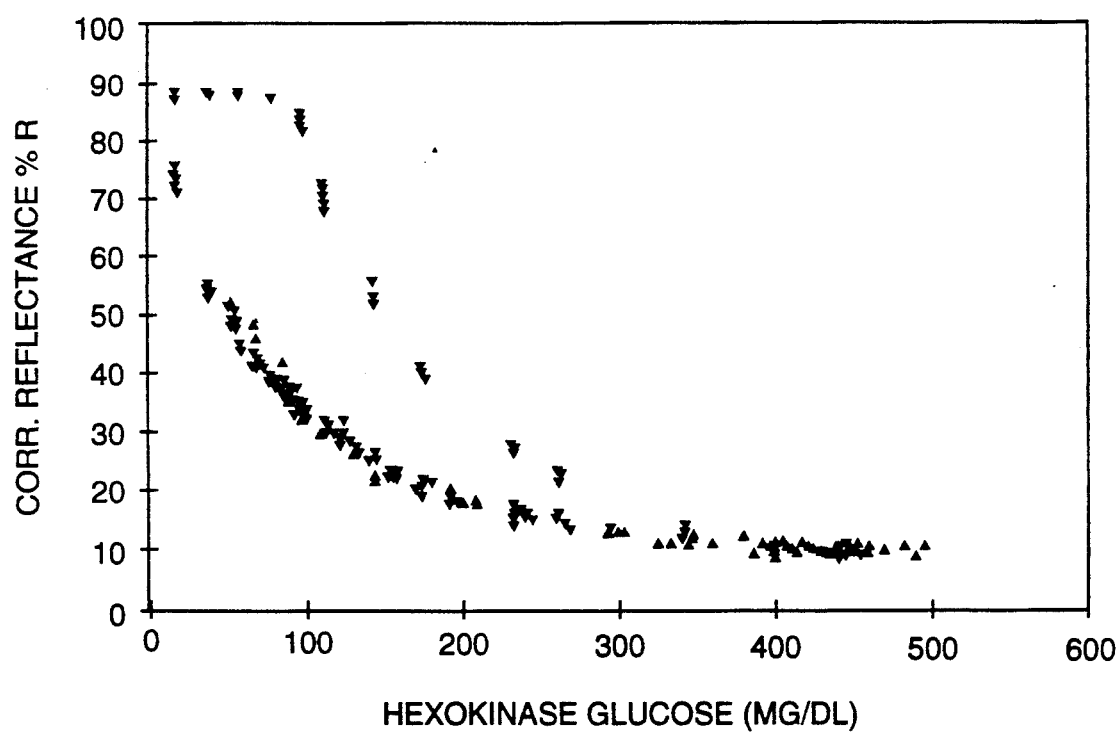
FIG. 2 shows a correlation curve when the control reagent is plasma based.

This material was then combined with N,N-dimethyl hydroxylamine. HCl (10 mg/dl), and tested against blood samples, as in Example 1. FIG. 2 presents the correlation curve obtained for this material, and indicates that the plasma control was very similar to capillary blood.

EXAMPLE 3

Figure 3:
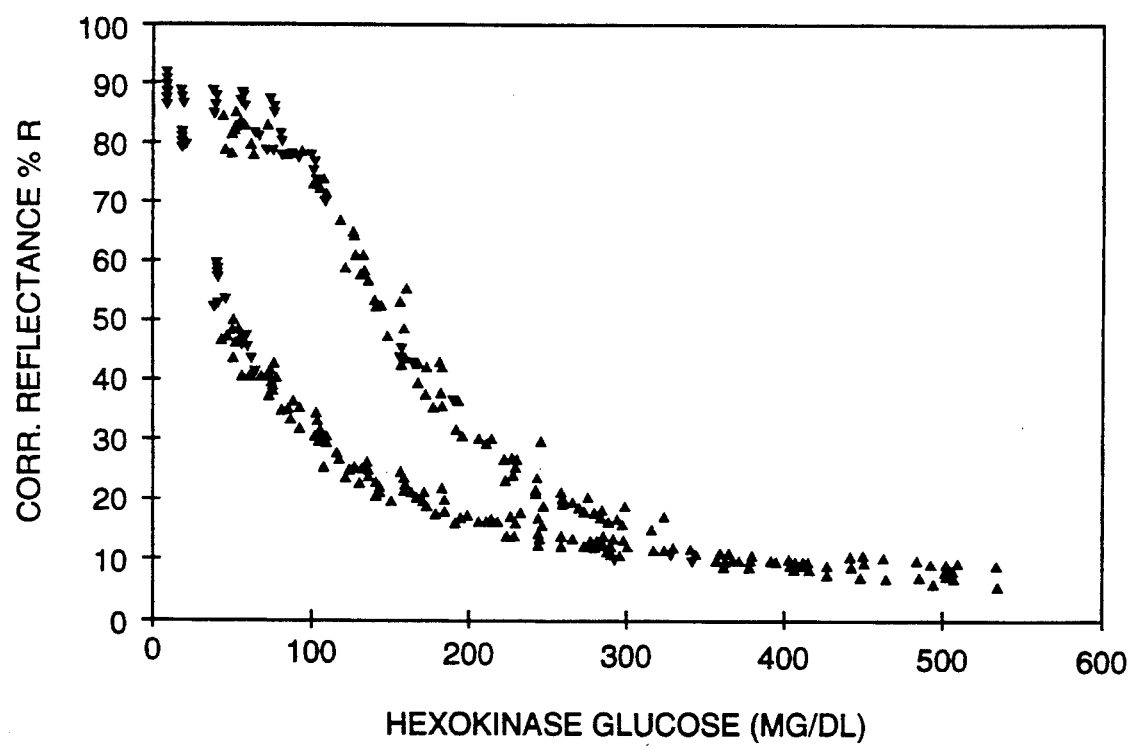
FIG. 3 depicts correlation between blood and a synthetic, serum free control reagent.

A control reagent was prepared by mixing 47.5 g of SERASUB, 2.5 g MES/CAPS (ratio of 8%:92%), and 0.015 g of N-(tert-butyl) hydroxylamine hydrochloride (final concentration: 30 mg/dl). This formulation was tested against capillary blood, and the results are presented in FIG. 3. Again, there is good correlation between blood and the control.

EXAMPLE 4

Figure 4:
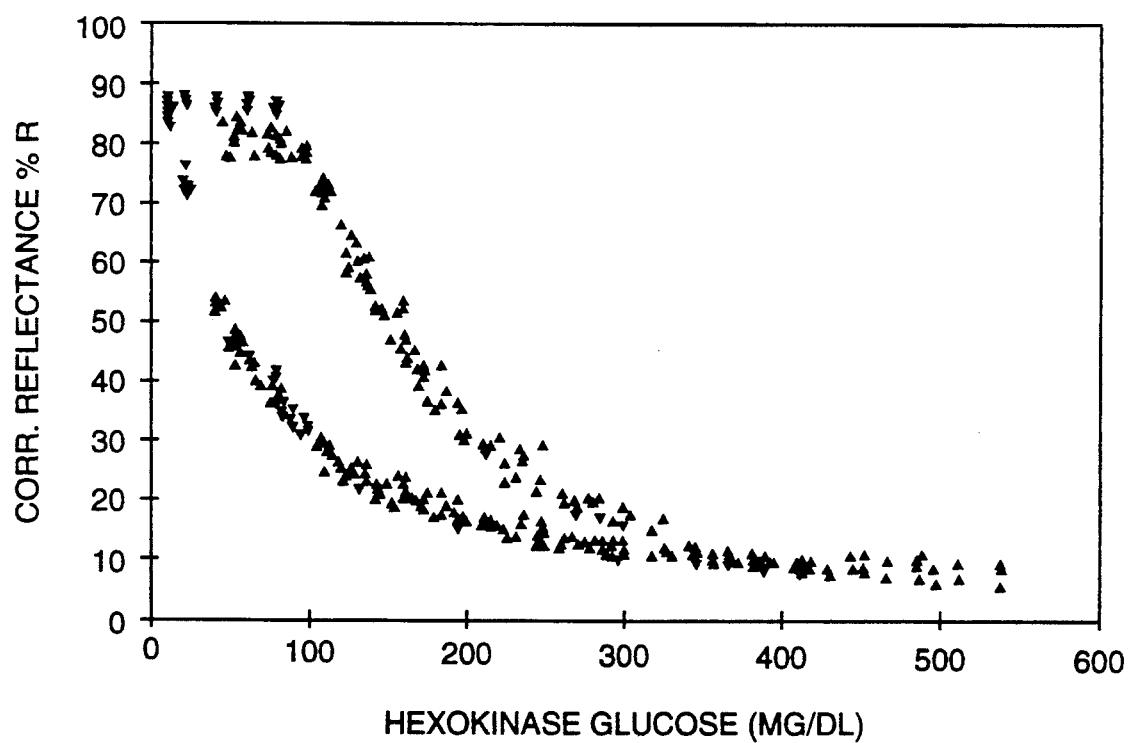
FIG. 4 shows correlation when a serum free control was stressed.

In order to test the stability of the control reagent of example 3, a similar formulation was prepared. Specifically, 190 g of SERASUB, 10 g of 1M MES/CAPS, and 0.24 g of N-(tert-butyl) hydroxylamine hydrochloride were combined, and stressed by being subjected to a temperature of 55° C. for three days. The stressed reagent was tested against capillary blood, and FIG. 4 shows the results. These indicate that notwithstanding the temperature stress, the control reagent remained useful.

EXAMPLE 5

Figure 5:
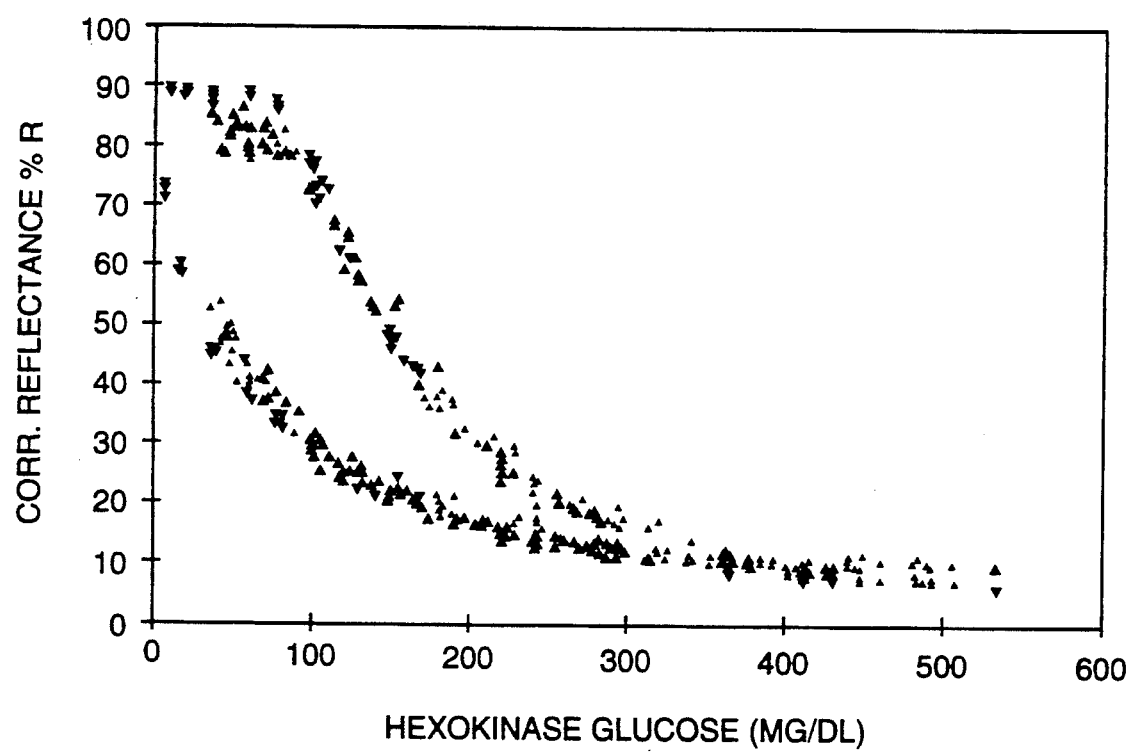
FIG. 5 also shows correlation following stress.

The limits of stability for the control reagents were tested, by subjecting the formulation described supra to 9-10 days of stress at 55° C. FIG. 5 shows that it was only after this severe stress that the correlation began to diverge.

EXAMPLE 6

Figure 6:
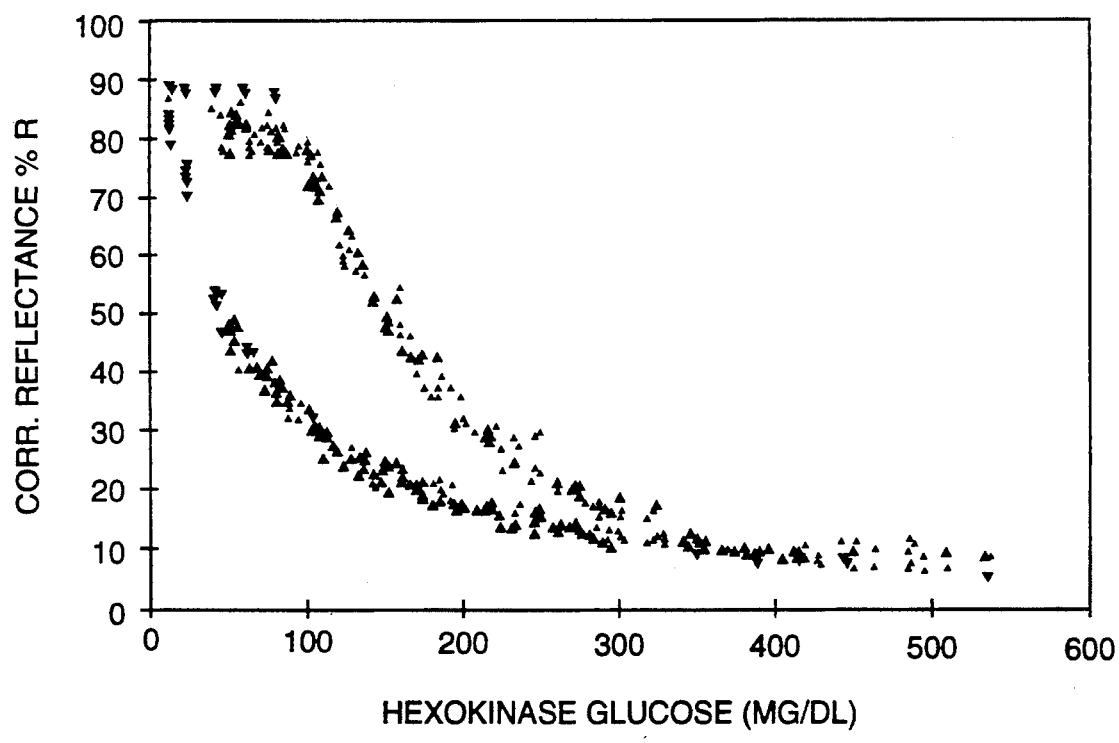
FIG. 6 also shows correlation following stress.

A similar test was carried out, stressing the reagent by subjecting it to room temperature for 9 days. FIG. 6 shows that the stress did not lead to significant problems with correlation.

The foregoing examples show that control reagents can be prepared which contain a carrier, a known amount of an analyte of interest, as well as an additive selected from the group consisting of a hydroxylamine and an antioxidant. "A hydroxylamine" as the term is used herein refers to any compound which contains the hydroxylamine group. As such, the class of compounds may be depicted as RNHOH, where R may be substituted as desired. For example, when "R" is hydrogen, the compound is hydroxylamine. Other compounds encompassed by the invention include N-(tert-butyl) hydroxylamine, O-tert butyl hydroxylamine, O-benzyl hydroxylamine, N,O-dimethyl-hydroxylamine, N,N-dimethylhydroxylamine, and N,N-diethylhydroxylamine. Also encompassed by the designation are hydroxylamine salts, acid addition salts such as the HCl and $H_2SO_4$ salts, being preferred.

"Antioxidant" as used herein, refers broadly to the class of compounds and substances which prevent the formation of compounds such as peroxides, ketones, aldehydes and acids from materials which do not contain these group in their monomeric state. Antioxidants are used because, in practice, a reaction of the following type is desired in the systems used in clinical analysis:

RH ⟶ R.

R. + $O_2$ ⟶ R—O—O.

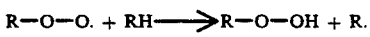

R—O—O. + RH ⟶ R—O—OH + R.

wherein "R" is the reactant of interest. Undesirable reactions which take place include:

R. + R. ⟶ R—R and

R—O—O. ⟶ R—O—O—R.

Antioxidants prevent the latter reaction from occurring, via interfering with the reaction:

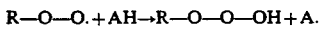

R—O—O. + AH → R—O—O—OH + A.

Among the oxidants which function in the way described are "BHA" (3-tertiary butyl 4-hydroxy anisole), "BHT" (2,6-ditertiary-butyl 4-methyl phenol), "TBHQ" (2-(1,1-dimethyl)-1,4-benzenediol), "PQ" (propyl gallate, i.e., 3,4,5 trihydroxyl benzoic acid), and the tocopherol family of molecules, i.e., Vitamin E and its derivatives. The choice of carrier is one that is left to the artisan. As has been indicated by the discussion, supra, control reagents may be based, e.g., on plasma, serum, blood, water, or other fluid materials. When a biological sample is used as the carrier (e.g., plasma), human source material is preferred, although other mammalian materials, such as bovine plasma or serum, may be used. The control reagents need not be prepared in solution form, however, as it is possible to prepare, e.g., suspensions or emulsions by adding materials to the other components listed above. Polymers and copolymers may be combined with the other ingredients listed above to create such suspensions or emulsions. It is also possible to have liquid free formulations of the control reagents, such as lyophilisates, powders, tablets, and so forth. The control reagent may also be incorporated into a test carrier or other form of analytical apparatus, if desired. Additional ingredients may also be added to the control reagent as desired. These may include preservatives, biocides, viscosity agents such as polystyrene sulfonate, buffers, dyes, and so forth. Other additives may be combined with the active ingredients as well, as is represented by the state of the art with respect to control reagents. These will be well known to the skilled artisan.

It will be understood that the specification and examples are illustrative but not limitative of the present invention and that other embodiments within the spirit and scope of the invention will suggest themselves to those skilled in the art.

We claim:

1. Control reagent useful in determining an analyte selected from the group consisting of glucose and cholesterol, consisting essentially of
   (i) a known amount of glucose or cholesterol;
   (ii) an additive selected from the group consisting of
      (a) a hydroxylamine group containing compound;
      (b) 2,6-ditertiarybutyl 4-methyl phenol; (c) 2-(1,1-dimethyl)-1,4-benzenedial; (d) 3,4,5-trihydroxylbenzoic acid; (e) vitamin E and (f) a vitamin E derivative, and
   (iii) a fluid carrier material.

2. The control reagent of claim 1, wherein said additive is a hydroxylamine group containing compound.

3. The control reagent of claim 2, wherein said hydroxylamine group containing compound is selected from the group consisting of hydroxylamine, N-(tert-butyl) hydroxylamine, O-tert butyl hydroxylamine, O-benzyl hydroxylamine, N,O-dimethyl-hydroxylamine, N,N-dimethylhydroxylamine, N,N-dimethylhydroxylamine, N,N-diethyl hydroxylamine, and acid salts thereof.

4. The control reagent of claim 1, wherein said analyte is glucose.

5. The control reagent of claim 1, wherein said analyte is cholesterol.

6. The control reagent of claim 1, wherein said fluid carrier material is serum.

7. The control reagent of claim 1, wherein said fluid carrier material is plasma.

8. The control reagent of claim 1, wherein said carrier material is water.

9. The control reagent of claim 3, wherein said hydroxylamine control is N-tert butyl hydroxylamine.

10. The control reagent of claim 3, wherein said hydroxylamine group containing compound is N,N-dimethylhydroxylamine.

11. The control reagent of claim 1, wherein said control reagent also contains a viscosity agent.

12. The control reagent of claim 1, wherein said control reagent also contains a preservative.

13. The control reagent of claim 1, wherein said control reagent also contains a biocide.

14. The control reagent of claim 1, wherein said control reagent also contains a buffer.

15. The control reagent of claim 1, in the form of an emulsion.

16. The control reagent of claim 1, wherein said additive is (a) 2,6-ditertiarybutyl 4-methyl phenol; (b) 2-(1,1-dimethyl)-1,4-benzenedial; (c) 3,4,5-trihydroxylbenzoic acid; (d) vitamin E (e) a vitamin E or (f) a vitamin E derivative.

17. Lyophilized control reagent useful in determining an analyte selected from the group consisting of glucose and cholesterol, consisting essentially of:
   (i) a known amount of glucose or cholesterol; and
   (ii) an additive selected from the group consisting of
      (a) a hydroxylamine group containing compound;
      (b) 2,6-ditertiarybutyl 4-methyl phenol; (c) 2-(1,1-dimethyl)-1,4-benzenedial; (d) 3,4,5-trihydroxylbenzoic acid; (e) vitamin E and (f) a vitamin E derivative.

* * * * *